United States Patent [19]

Downs

[11] Patent Number: 4,752,580

[45] Date of Patent: Jun. 21, 1988

[54] PROCESS FOR PREPARING XANTHOMONAS HETEROPOLYSACCHARIDES

[75] Inventor: John D. Downs, Sittingbourne, England

[73] Assignee: Shell Oil Company, Houston, Tex.

[21] Appl. No.: 626,169

[22] Filed: Jun. 29, 1984

[30] Foreign Application Priority Data

Jun. 29, 1983 [GB] United Kingdom ............ 8317696

[51] Int. Cl.$^4$ ............................................. C12P 19/06
[52] U.S. Cl. ..................................... 435/104; 435/101; 435/253; 435/813; 435/910; 536/114; 536/123
[58] Field of Search ............... 435/104, 910, 813, 101, 435/253; 536/114, 123

[56] References Cited

U.S. PATENT DOCUMENTS

| | | | |
|---|---|---|---|
| 4,104,123 | 8/1978 | Duc et al. ............................ | 195/31 |
| 4,301,247 | 11/1981 | Weisrock ........................... | 435/104 |
| 4,311,796 | 1/1982 | Weisrock ........................... | 435/104 |
| 4,328,308 | 5/1982 | Weisrock ........................... | 435/104 |
| 4,418,145 | 11/1983 | Weisrock et al. ................... | 435/910 |

*Primary Examiner*—Charles F. Warren
*Assistant Examiner*—David S. Kaplan

[57] ABSTRACT

Process for preparing Xanthomonas heteropolysaccharide from *Xanthomonas campestris* NCIB 11854 and use of the latter, e.g. as viscosity modifier in an aqueous solution, and in a drilling fluid and use in connection with well treatments, and enhanced oil recovery.

6 Claims, 3 Drawing Sheets

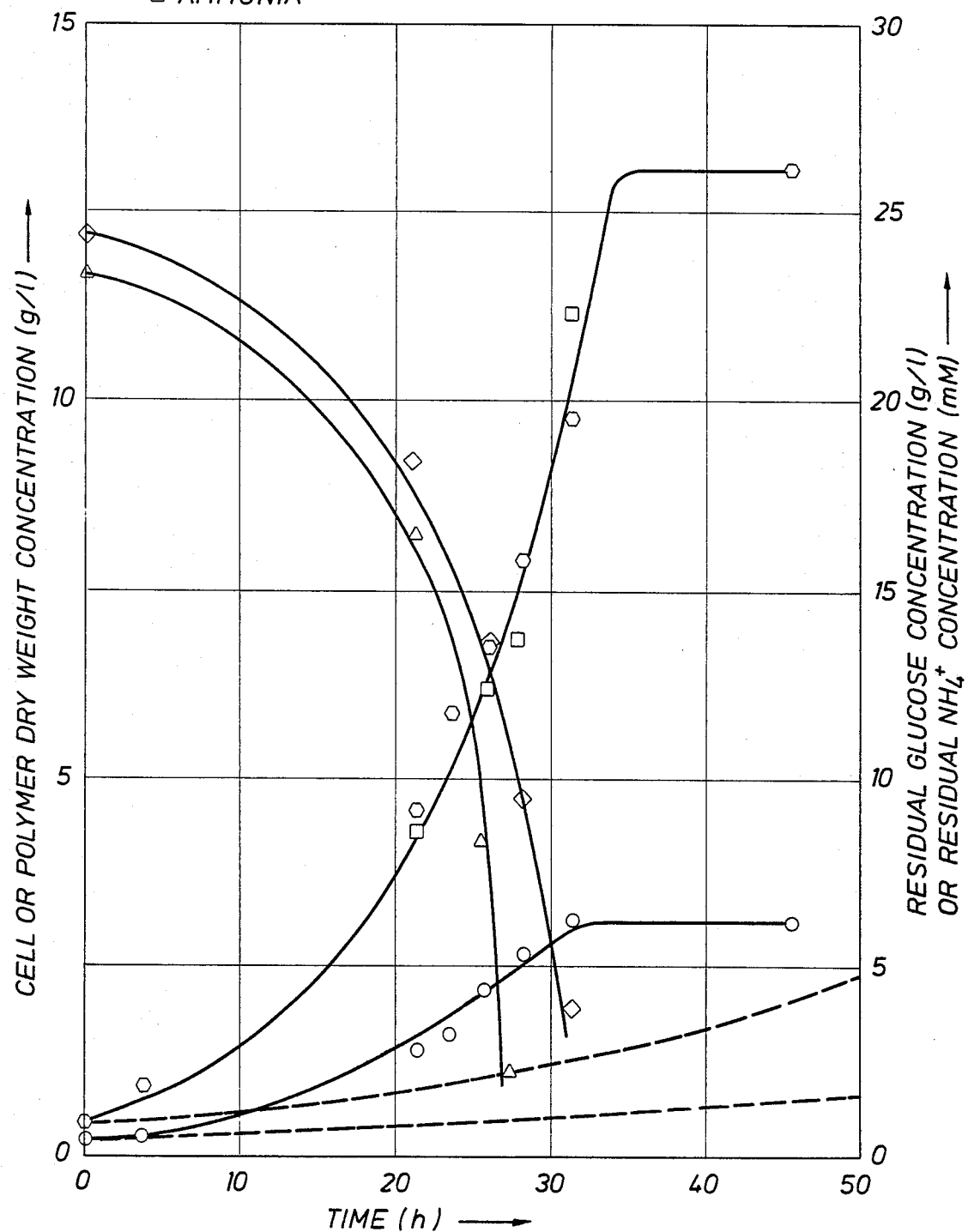
FIG.1 GROWTH AND POLYMER PRODUCTION BY X. CAMPESTRIS NCIB 11854 (SOLID LINES) AND X. CAMPESTRIS NRRL B-1459 (DASHED LINES: TOP, POLYMER; BOTTOM, CELLS) IN DEFINED SALTS MEDIUM (1) AMONIA AS NITROGEN SOURCE.

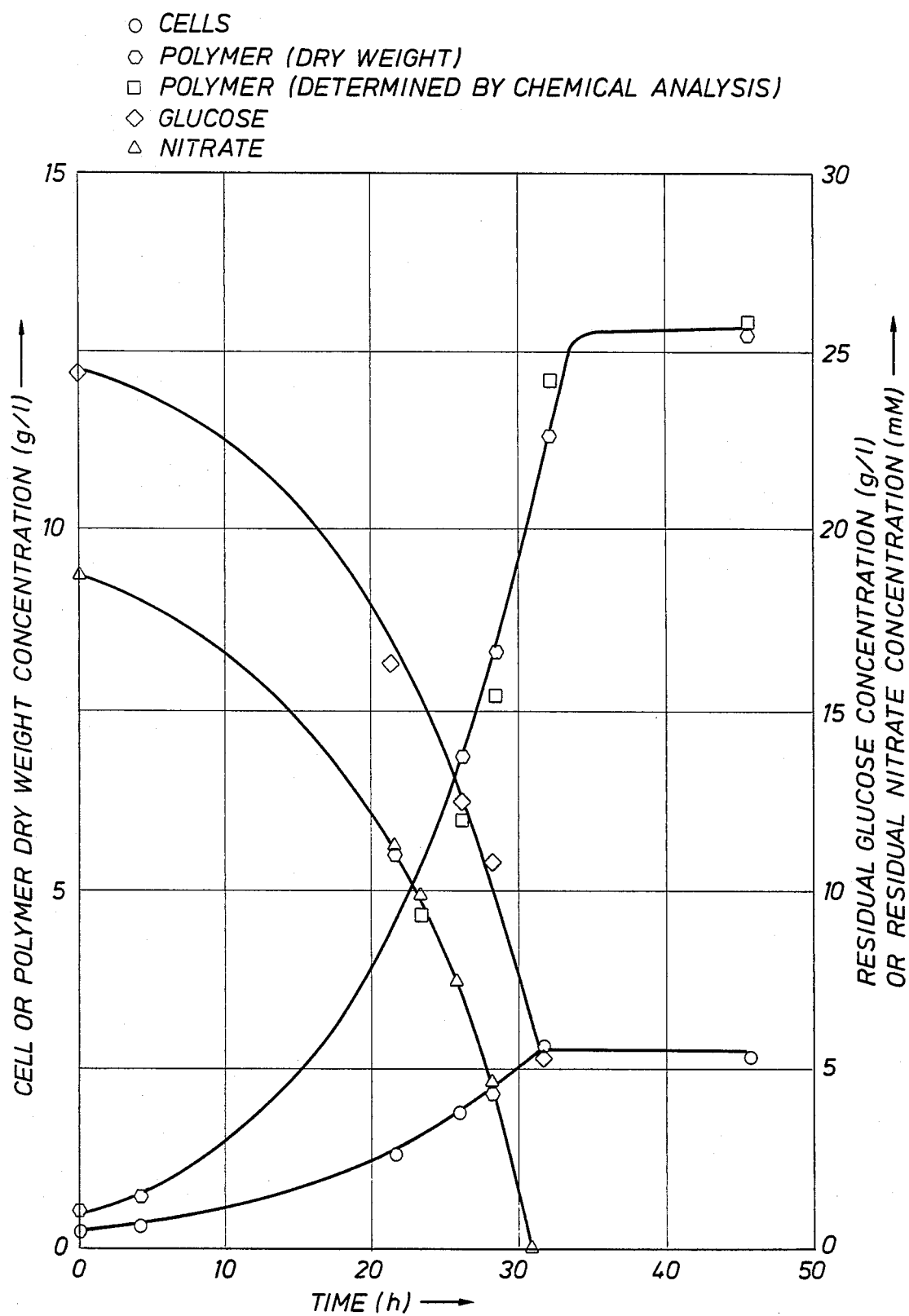
FIG.2 GROWTH AND POLYMER PRODUCTION BY X.CAMPESTRIS NCIB 11854 IN DEFINED SALTS MEDIUM (2) NITRATE AS NITROGEN SOURCE.

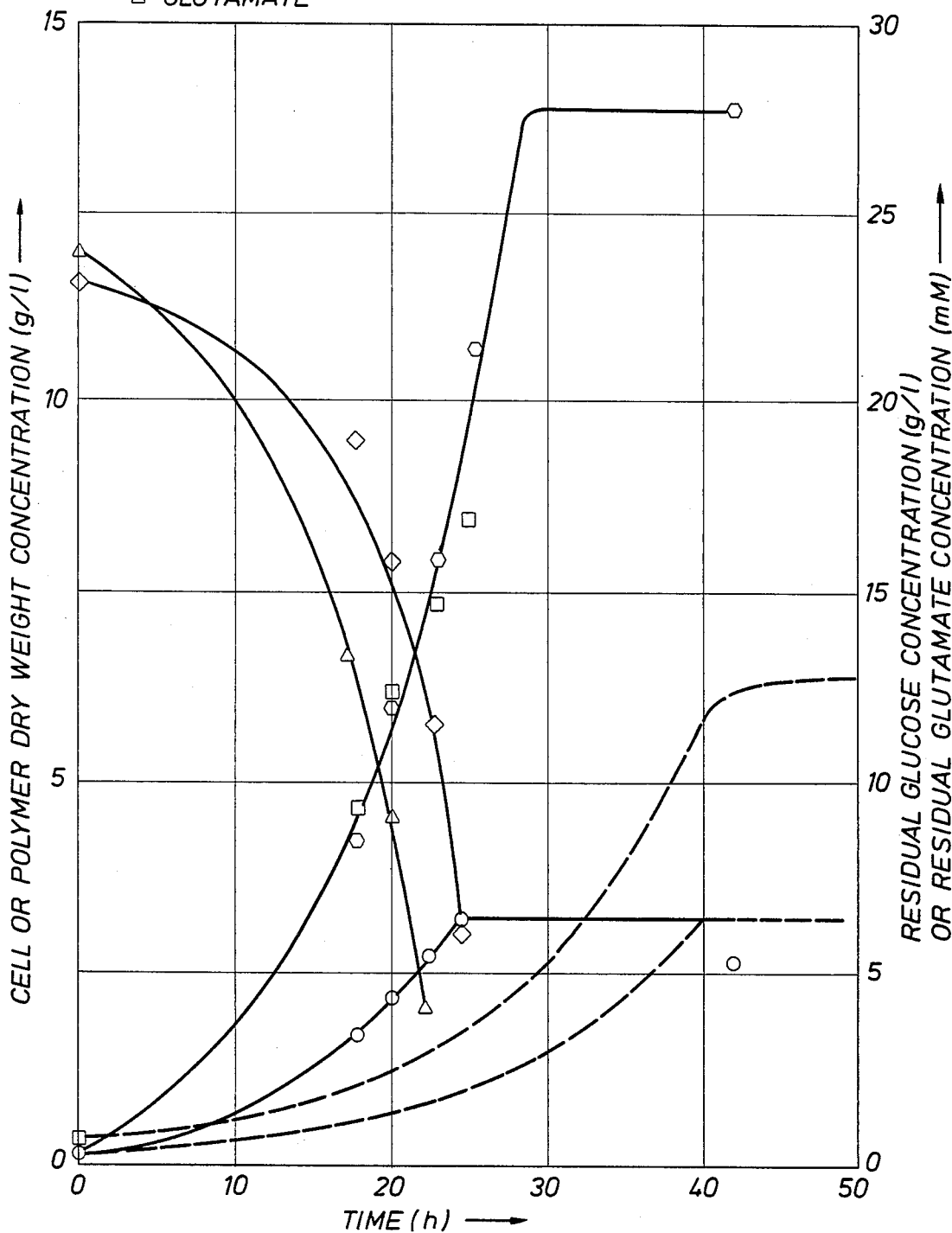
FIG.3 GROWTH AND POLYMER PRODUCTION BY X.CAMPESTRIS NCIB 11854 (SOLID LINES) AND X.CAMPESTRIS NRRL B-1459 (DASHED LINES: TOP, POLYMER; BOTTOM, CELLS) IN DEFINED SALTS MEDIUM (3) GLUTAMATE AS NITROGEN SOURCE.
○ CELLS
○ POLYMER (DRY WEIGHT)
□ POLYMER (DETERMINED BY CHEMICAL ANALYSIS)
◇ GLUCOSE
△ GLUTAMATE

PROCESS FOR PREPARING XANTHOMONAS HETEROPOLYSACCHARIDES

BACKGROUND OF THE INVENTION

1. Field of the Invention

The present invention relates to a process for preparing Xanthomonas heteropolysaccharides by fermenting a certain Xanthomonas species.

2. Description of the Prior Art

From U.S. Pat. No. 3,485,719 it is known that heteropolysaccharides can be prepared by subjecting a carbohydrate source to fermentation by the organism *Xanthomonas campestris* NRRL B-1459. In this patent specification it is stated that the heteropolysaccharide produced from *Xanthomonas campestris* NRRL B-1459 has been shown to be an exceptionally effective agent when used in secondary oil recovery operations as well as exhibiting utility as a thickening agent for foodstuffs, cosmetics, etc., and also as an edible film-forming agent, and as an emulsifying agent, for example, in printing ink and as thickening agent in textile print pastes.

SUMMARY OF THE INVENTION

Applicant has now isolated a novel substrain of *Xanthomonas campestris* species which has been deposited at the National Collection of Industrial Bacteria, Torry Research Station, Aberdeen, under accession No. 11854. Compared with the microorganism *Xanthomonas campestris* NRRL B-1459, the present microorganism, NCIB 11854 appears to exhibit a much higher specific growth rate in a defined medium coupled with a remarkably higher specific rate of polymer production.

Furthermore, the filterability of the heteropolysaccharide produced by the NCIB 11854 microorganism is as good as or is even better than that of the heteropolysaccharide produced by the *Xanthomonas campestris* NRRL B-1459, especially at higher salinities. The present invention therefore provides a process for preparing Xanthomonas heteropolysaccharide which comprises growing the organism *Xanthomonas campestris* NCIB 11854 in an aqueous nutrient medium by aerobic fermentation of an assimilable carbohydrate and nitrogen source and recovering the heteropolysaccharide. The process may suitably be carried out as a batch-process or a fed-batch process with or without fill-and-draw or as a continuous process.

From productivity considerations a continuous process or a fill-and-draw process is preferred. Preferably, the organism is grown in the absence of yeast extract in a nutrient medium. The use of a chemically defined nutrient medium is advantageous since for a given productivity or for a given final cell concentration it appears easier to handle a nitrogen source such as sodium glutamate, ammonium or nitrate salts than complex nitrogen sources such as yeast extract or distillers dried solubles. Sodium glutamate is preferably used as a nitrogen source. The present invention further relates to the heteropolysaccharide as prepared by the process as hereinbefore described and to the use of the heteropolysaccharide as viscosity modifier in an aqueous solution for various conventional utilities.

A drilling fluid comprising water and 0.06–1.5% by weight of the above heteropolysaccharide is a further aspect of the present invention. The present invention also encompasses a method of treating a well comprising the introduction into the well of an aqueous medium comprising water and 0.05–1.5% by weight of the above heteropolysaccharide as well as a method for displacing a fluid through a well and/or a permeable subsurface formation communicating with the well by injecting into the well an aqueous solution comprising the above heteropolysaccharide. The present invention further relates to a biologically pure culture of *Xanthomonas campestris* NCIB 11854.

The present invention will now be further illustrated by the following Example.

EXAMPLE

Preparation of Heteropolysaccharide by Cultivation of *Xanthomonas campestris* sp. NCIB 11854 and a Comparison of Its Performance with that of *Xanthomonas campestris* NRRL B-1459

*Xanthomonas campestris* NCIB 11854 was grown on three different chemically defined salt media (as shown in Table 1) in a Chemap GF 7 liter fermentation vessel under batch conditions as summarized in Table 2.

TABLE 1

CHEMICALLY DEFINED SALTS MEDIUM FOR THE CULTURE OF *XANTHOMONAS CAMPESTRIS* NCIB 11854

| Component | Concentration (mM)[a] | | |
|---|---|---|---|
| | Medium 1 | Medium 2 | Medium 3 |
| Glucose | 24.5 (gl$^{-1}$)[b] | 24.3 (gl$^{-1}$) | 23.4 (gl$^{-1}$) |
| (NH$_4$)$_2$SO$_4$ | 12 (24 mM N)[c] | — | — |
| NaNO$_3$ | — | 24 | — |
| Na Glutamate | — | — | 24 |
| KH$_2$PO$_4$ | 25 | 25 | 25 |
| Na$_2$HPO$_4$ | 25 | 25 | 25 |
| MgSO$_4$.7H$_2$O | 2 | 2 | 2 |
| CaCl$_2$.2H$_2$O | 1 | 1 | 1 |
| FeSO$_4$.7H$_2$O | 0.2 | 0.2 | 0.2 |
| MnSO$_4$.7H$_2$O | 20 × 10$^{-3}$ | 20 × 10$^{-3}$ | 20 × 10$^{-3}$ |
| CuSO$_4$.5H$_2$O | 20 × 10$^{-3}$ | 20 × 10$^{-3}$ | 20 × 10 |
| CoCl$_2$.6H$_2$O | 10 × 10$^{-3}$ | 10 × 10$^{-3}$ | 10 × 10$^{-3}$ |
| H$_3$BO$_3$ | 10 × 10$^{-3}$ | 10 × 10$^{-3}$ | 10 × 10$^{-3}$ |
| Na$_2$MoO$_4$.2H$_2$O | 10 × 10$^{-3}$ | 10 × 10$^{-3}$ | 10 × 10$^{-3}$ |
| KI | 10 × 10$^{-3}$ | 10 × 10$^{-3}$ | 10 × 10$^{-3}$ |

[a]mM = millimolar.
[b]gl$^{-1}$ = grams/liter
[c]mM = millimolar nitrogen.

TABLE 2

GROWTH CONDITIONS FOR THE CULTURE OF *XANTHOMONAS CAMPESTRIS* NCIB 11854

| | |
|---|---|
| Temperature | 28° C. |
| pH | 6.8 |
| Impeller | 3 × 4 Bladed Rushton turbine |
| Impeller speed | 1000 rpm |
| Culture volume | 4.5–5.0 liters |
| pH control | 1N NaOH + 1N KOH |
| Dissolved O$_2$ tension | >80 mm Hg |
| Air flow rate | 1.0 liters/minute |

In the first experiment the sole source of nitrogen for microbial growth was ammonium ion (24 mM), allowing exponential growth of cells to a maximum concentration of 3 gl$^{-1}$. In the second and third experiments the ammonium was substituted with nitrate (24 mM) and glutamate (24 mM) respectively. The results are shown in FIGS. 1-3.

As is clear from a comparison of these figures, glutamate as a nitrogen source is preferred since it gives a μmax, i.e. maximum cell growth rate of 0.12 h$^{-1}$, a qp value, i.e. specific rate of polymer production of 0.36 g.(g$^{-1}$)h$^{-1}$ and a final polymer yield Yp of 0.59 g.g$^{-1}$. This combination of high μmax and high qp resulted in a final polymer productivity of 0.49 g.(l$^{-1}$)h$^{-1}$, which is more than double the normal productivity of a heteropolysaccharide fermentation using *Xanthamonas campestris* NRRL B-1459.

Table 3 indicates under A the values of $\mu$max, qp, qg, i.e. the specific glucose utilization rate, Yp, i.e. yield of polymer on glucose and p, i.e. polymer productivity for *Xanthomonas campestris* NCIB 11854 on the above defined salts growth medium and under B the respective values for *Xanthomonas campestris* NRRL B-1459.

TABLE 3

KINETIC DATA FROM THE CULTURE OF *XANTHOMONAS CAMPESTRIS* NCIB 11854 (A) AND *XANTHOMONAS CAMPESTRIS* NRRL B-1459 (B) ON DEFINED SALTS GROWTH MEDIUM

| Run | Nitrogen Source | $\mu$max (h$^{-1}$) | qp [g(g$^{-1}$)h$^{-1}$] | qg [g(g$^{-1}$)h$^{-1}$] | Yp [g(g$^{-1}$)] | p [g(l$^{-1}$)h$^{-1}$] |
|---|---|---|---|---|---|---|
| A | | | | | | |
| 1 | Ammonia | 0.09 | 0.275 | 0.60 | 0.53 | 0.39 |
| 2 | Nitrate | 0.084 | 0.35 | 0.60 | 0.52 | 0.38 |
| 3 | Glutamate | 0.12 | 0.36 | 0.68 | 0.59 | 0.49 |
| B | | | | | | |
| 1 | Ammonia | 0.03 | 0.08 | ? | 0.51 | 0.13 |
| 2 | Glutamate | 0.07 | 0.11 | ? | 0.41 | 0.21 |

This table clearly shows the better performance of *Xanthomonas campestris* NCIB 11854 compared with *Xanthomonas campestris* NRRL B-1459.

In Table 4 the filterability of *Xanthomonas campestris* NCIB 11854 broth is compared with that of *Xanthomonas campestris* NRRL B-1459 broth for different salinities of the medium before and after enzyme treatment.

TABLE 4

FILTERABILITY OF 20cP SOLUTIONS$^{(a)}$

| Strain | Sample | Filtration Time (sec) for 200 ml 5$\mu$ + P/F$^{(b)}$ | 1.2$\mu^{(c)}$ |
|---|---|---|---|
| A. In 1% NaCl + 0.1% CaCl$_2$ at 30° C., 1 atm over pressure | | | |
| NCIB 11854 | Broth | 11.0 | 63.0 |
| | Enzyme treat. | 9.5 | 29.3 |
| NRRL B-1459 | Broth | 17.5 | 59.6 |
| | Enzyme treat. | 19.0 | 188.0 |
| B. In 1% NaCl + 0.1% CaCl$_2$ at 70° C., 1 atm overpressure | | | |
| NCIB 11854 | Broth | 7.5 | 37.3 |
| | Enzyme treat. | 5.5 | 17.0 |
| NRRL B-1459 | Broth | 35.8 | 50.7 |
| | Enzyme treat. | 8.5 | 40.9 |
| C. In 15% NaCl + 1.5% CaCl$_2$ at 30° C., 1 atm overpressure | | | |
| NCIB 11854 | Broth | 14.5 | 330 |
| | Enzyme treat. | 22.1 | 101 |
| NRRL B-1459 | Broth | 30.8 | 81.7 |
| | Enzyme treat. | >1000 | >1000 |
| D. In 15% NaCl + 1.5% CaCl$_2$ at 70° C., 1 atm overpressure | | | |
| NCIB 11854 | Broth | 17.0 | 299 |
| | Enzyme treat. | >1000 | >1000 |
| NRRL B-1459 | Broth | >1000 | >1000 |

$^{(a)}$Viscosity measured at 7.5 sec shear rate, 30° C.
$^{(b)}$P/F = Prefilter for separation of coarse material.
$^{(c)}$Without Prefilter.

For the actual filtration, Millipore (trade mark) filters having a diameter of 47 mm have been used. 5$\mu$ and 1.2$\mu$ are sizes of the pores of these filters. As is clear from the above table, the filterability of *Xanthomonas campestris* NCIB 11854 broth before and after enzyme treatment is remarkably better than that of *Xanthomonas campestris* NRRL B-1459.

Characterisation by the National Collection of Industrial Bacteria of *Xanthomonas campestris* NCIB 11854 and *Xanthomonas campestris* NCIB 11803=NRRL B-1459, hereafter referred to as NCIB 11854 and NCIB 11803 respectively.

The results were similar for NCIB 11803 and NCIB 11854 except where stated

Cell Morphology

A. Oxoid CMI Nutrient Broth+0.75% Difco Agar plates were inoculated with 'young' growth and incubated for 7½ hours at 25° C. Cells from the margins of c. 0.2 mm patches of growth were examined and photographed in situ under coverslips by phase-contrast. Mobility and the other features were determined in pools surrounding 0.1 mm glass beads scattered on other patches. Cells at the margins of growth occurred singly and in pairs, with cell dimensions of 0.4–0.5 $\mu$m width $\times$ 1.2–2.5 $\mu$m length for NCIB 11803 and 0.5–0.6 $\mu$m $\times$ 1.2–2.5 $\mu$m for NCIB 11854. In from the growth margin in pools, aggregates (symplasmata). See Graham & Hodgkiss, 1967) of a hundred to several thousand cells were commonly seen with NCIB 11803 but much less frequently with NCIB 11854. Mobility was positive.

B. Using conditions as in A above but with 0.5% glucose added to the medium and 7 hours incubation result were similar except that cells were 0.1 $\mu$m wider and aggregates were not seen with NCIB 11854.

Colony Morphology

A. After 48 hours growth at 30° C. on Oxoid CM3 Nutrient Agar plates growth was good, and isolated colonies were yellow in colour, circular, entire, mucoid, smooth, string and convex. Colony diameter was 1–1.5 mm for 11803 and 1.5 mm for NCIB 11854.

B. After 72 hours growth at 30° C. on medium as in A above but with 1% glucose growth was good and isolated colonies were pale cream in colour, circular, entire, very mucoid, smooth and convex, while confluent growth was pale cream-yellow. Colony diameter was 2 mm for NCIB 11803 and 2–2.5 mm for 11854.

Selected Morphology

Mineral Base Palleroni 6 Doudoroff 1972 Modified (PD) (A. Rev. Phytophetol. 10, 73)

| | |
|---|---|
| Na$_2$HPO$_4$ 12H$_2$O | 6.0 g |
| KH$_2$PO$_4$ | 2.4 g |
| NH$_4$Cl | 1.0 g |
| MgSO$_4$.7H$_2$O | 0.5 g |
| FeCl$_3$.6H$_2$O | 0.01 g |
| CaCl$_2$.6H$_2$O | 0.01 g |
| Deionized water | 1 liter |
| the ptt will be 6.8 | |

PD Mineral Base+0.1% Filter-Sterilized Glucose (PDG)

| Gelatin Stabs | |
|---|---|
| Nutrient Broth No. 2 (Oxoid) | 2.5% |
| Gelatin (Difco) | 12.0% |

| -continued | |
|---|---|
| Gelatin Plates | |
| Nutrient Agar Oxoid CM3 | 2.8% |
| Gelatin | 1.0% |
| Milk Plates | |
| Skim Milk (Difco) Separately sterilised | 3% |
| Peptone (Difco) | 0.1% |
| Beef Extract Lab-Lemco | 0.1% |
| NaCl | 0.5% |
| Agar | 1.5% |
| pH 7.4 before autoclaving | |

Biochemical Characteristics: at 30° C. except as stated
Growth at °C. on CM3 Plates

| Temperature | 5° | 30° | 37° |
|---|---|---|---|
| Growth (non-quantitative) | + | + | − | pH Growth Range on CMI broth (adjusted pH)

| pH | 3 | 5 | 7.2 | 8 | 9 | 10 |
|---|---|---|---|---|---|---|
| Growth | − | 3+ | 3+ | 3+ | 3+ | 3+ |

Growth in Presence of Salt

Basal media containing NaCl at concentrations of 2, 3, 4 and 5% were prepared according to the method of Hayward & Hodgkiss (1961). Cultures were incubated for 3 days.
NCIB 11854 was less salt tolerant than NCIB 11803 as follows

| NaCl % | 2 | 3 | 4 | 5 |
|---|---|---|---|---|
| NCIB 11803 growth | 3+ | 3+ | 3+ | − |
| NCIB 11854 growth | 3+ | 3+ | + | − |

Hydrolysis of Gelatin and Casein

Cultures were incubated for 7 days. Gelatin stabs were at 20° C. NCIB 11854 showed a lesser degree of proteolytic activity than NCIB 11803 as follows

| | Gelatin Stab | Gelatin Plate | Milk Plate |
|---|---|---|---|
| NCIB 11803 | + | + | + |
| NCIB 11854 | − | + | weak + |

Growth Factor Requirement Tests

Subcultures were made by straight wire three times in PDG medium made with glass distilled water. Satisfactory growth was obtained in about 4 days indicating there was no absolute requirement for growth factors.

Methionine Stimulation Test

One drop each of a faintly turbid young growing culture in PDG medium made with glass distilled water was inoculated into PDG with and without 10 μg/ml L-methionine in 1 ml amounts in 16 mm tubes. There was no stimulation of the growth rate by L-methionine.

Carbon Source Utilization

PD medium with 0.1% filter-sterilized sole carbon sources shown in Table 1 were inoculated and incubated for 14 days. Three apparently minor differences in growth between the strains were found.

Acid Production from Carbohydrates

The oxidation-fermentation medium of Hayward and Hodgkiss (1961) was supplemented with 1% filter-sterilized carbon sources shown in Table 1. The tubes were inoculated and incubated for 14 days. Acid was produced from galactose and melibiose by NCIB 11854 but not by NCIB 11803. The significance of this is doubtful particularly because both compounds were utilized as sole carbon sources by both NCIB 11854 and NCIB 11803.

| | Acid production from O—F medium | | Growth from sole carbon source | |
|---|---|---|---|---|
| | NCIB 11803 | NCIB 11854 | NCIB 11803 | NCIB 11854 |
| Carbohydrates and sugar derivates | | | | |
| D-Ribose | | | − | − |
| D-Xylose | trace | − | weak | weak |
| L-Arabinose | weak | weak | − | − |
| L-Rhamnose | | | − | − |
| D-Glucose | + | + | + | + |
| D-Fructose | + | + | + | + |
| Sucrose | + | + | + | + |
| Trehalose | + | + | + | + |
| Cellobiose | weak | + | + | + |
| 2-Ketogluconate | | | | |
| Saccharate | | | − | − |
| Fatty acids | | | | |
| Acetate | | | weak | weak |
| Propionate | | | − | − |
| Butyrate | | | − | − |
| Dicarboxylic acids | | | | |
| →Malonate | | | weak | <+ |
| Hydroxy acids | | | | |
| D (−)-Tartrate | | | − | − |
| meso-Tartrate | | | − | − |
| DL-3-Hydroxybutyrate | | | − | − |
| DL-Lactate | | | − | − |
| Glycollate | | | − | − |
| Miscellaneous organic acids | | | | |
| Levulinate | | | − | − |
| Citraconate | | | − | − |
| Mesaconate | | | − | − |
| Sugar Polyalcohols and glycols | | | | |
| Erythritol | | | − | − |
| Sorbitol | − | − | − | − |
| meso-Inositol | − | − | − | − |
| Adonitol | | | − | − |
| Propylene glycol | | | − | − |
| 2,3-Butylene glycol | | | − | − |
| D-Mannitol* | weak | + | − | <weak |
| Glycerol* | + | + | − | <weak |
| Alcohols | | | | |
| Methanol* | | | − | − |
| Ethanol | | | − | − |
| Geraniol | | | | |
| Non-nitrogenous aromatic and other cyclic compounds | | | | |
| meta-Hydroxybenzoate | | | − | − |
| para-Hydroxybenzoate | | | − | − |
| Testosterone | | | | |
| Aliphatic amino acids | | | | |
| L-Valine | | | − | − |
| L-Arginine+ | | | | |
| Amino acids containing a ring structure | | | | |
| Histidine | | | − | − |
| L-Tryptophan* | | | − | − |
| Anthranilate* | | | − | − |

-continued

| | Acid production from O—F medium | | Growth from sole carbon source | |
|---|---|---|---|---|
| | NCIB 11803 | NCIB 11854 | NCIB 11803 | NCIB 11854 |
| Amines | | | | |
| Benzylamine* | − | − | | |
| Tryptamine-Amylamine | | | | |
| Miscellaneous nitrogenous compounds | | | | |
| Betaine | | | | |
| Pantothenate | | | | |
| Carbohydrates and sugar dervitives continued | | | | |
| Galactose° | − | + | + | + |
| Mannose° | + | + | + | + |
| Lactose* | − | − | − | − |
| Maltose* | + | + | + | + |
| Melibiose* | − | + | + | + |

*Additional compound
+ In place of DL-

TABLE 2

| | Gram-negative non-fermentatives | | | | | | | |
|---|---|---|---|---|---|---|---|---|
| | Isolate NCIB | | | | | | | |
| °C. incubation | 11803 30 | 11854 30 | | 11803 30 | 11854 30 | | 11803 30 | 11854 30 |
| Pyocyanin | brown diffusible pigment | | Gas glucose | | | Growth at °C. | | |
| Fluorescence | in the culture broth | | ONPG | | | 5° | + | + |
| L-Arg CSU | | | Arg Moller | − | − | 30° | + | + |
| Betaine CSU | | | Lys Moller | | | 37° | − | − |
| Glucose CSU | | | Orn Moller | − | − | Growth at pH | | |
| | | | | | | 3 | − | − |
| Lactate CSU | | | NO⁻₃ to NO⁻₂ | − | − | 5 | 3+ | 3+ |
| Acetate CSU | | | NO⁻₃ to N₂ | − | − | 8 | 3+ | 3+ |
| | | | Residual NO₃ | + | + | 9 | 3+ | 3+ |
| Sensitivity | | | DNA ase | | | 10 | 3+ | 3+ |
| Penicillin G | − | − | Gel stab 20° | +7 | −7 | Growth in NaCl | | |
| Streptomycin | +++ | +++ | Gel plate | + | + | 2% | 3+ | 3+ |
| | | | | | | 3% | 3+ | 3+ |
| Chloramphen. | +++ | +++ | Casein | + | weak+ | 4% | 3+ | 3+ |
| Tetracycline | +++ | +++ | Starch | + | + | 5% | − | − |
| Novobiocin | + | + | Lecith egg | − | − | brown diffusible pigment | | |
| Polymyxin B | + | ++ | Lipase egg | − | − | in the tryprone uxiter culture | | |
| 0/129 | | | NH₃ | + | + | | | |
| Levan | | | Indole | − | − | | | |
| Growth factor | − | − | H₂S (TSI) + lead | − | − | | | |
| requirement | (glucose CSU) | (glucose CSU) | acetate paper | weak+ | weak+ | | | |
| Urease Christenson | − | − | Tween 80 MR | − | − | | | |
| Litmus milk | peptonised reduced | peptonised reduced | VP | − | − | | | |
| | | | Arg Thornley | − | − | | | |

These tests indicate limited differences so the main differences are that T.1188 exhibits better kinetics of polymer production in a defined medium, better growth with inorganic nitrogen, especially $NH_4+$ and stability in continuous culture in a defined medium.

References

1. Bergey's Manual of Determinative Bacteriology, 8th edn (1974). (R. E. Buchanan & N. E. Gibbons, eds). Baltimore: Williams & Wilkins.
2. Cowan, S. T. & Steel, K. J. (1974). Manual for the Identification of Medical Bacteria. Cambridge University Press.

What is claimed is:

1. A process for preparing *Xanthomonas campestris* heteropolysaccharide which comprises growing the organism *Xanthomonas campestris* NCIB 11854 in a chemically defined aqueous nutrient medium by aerobic fermentation of an assimilable carbohydrate and nitrogen source and recovering the heteropolysaccharide.

2. A process according to claim 1 wherein the process is carried out as a continuous process or as a fill and draw process.

3. A process according to claim 1 wherein the organism is grown in the absence of yeast extract.

4. A process according to claim 1 wherein glutamate is used as nitrogen source.

5. A heteropolysaccharide prepared by growing *Xanthomonas campestris* NCIB 11854 in a chemically defined aqueous nutrient medium by aerobic fermentation of an assimilable carbohydrate and nitrogen source and recovering the heteropolysaccharide.

6. The biologically pure culture of the *Xanthomonas campestris* NCIB 11854.

* * * * *